United States Patent [19]

Barfurth et al.

[11] Patent Number: 4,621,148

[45] Date of Patent: Nov. 4, 1986

[54] WATER-SOLUBLE TRIETHANOLAMINE TITANATES

[75] Inventors: Dieter Barfurth, Troisdorf-Spich; Heinz Nestler, Troisdorf-Eschmar, both of Fed. Rep. of Germany

[73] Assignee: Dynamit Nobel AG, Cologne, Fed. Rep. of Germany

[21] Appl. No.: 658,488

[22] Filed: Oct. 9, 1984

[30] Foreign Application Priority Data

Oct. 12, 1983 [DE] Fed. Rep. of Germany ....... 3337099

[51] Int. Cl.[4] .............................................. C07F 7/28
[52] U.S. Cl. .................. 556/54; 106/308 N; 106/308 Q; 528/17
[58] Field of Search ..................... 260/429.5; 556/54

[56] References Cited

U.S. PATENT DOCUMENTS

| | | | |
|---|---|---|---|
| 2,824,114 | 2/1958 | Bostwick | 260/429.3 |
| 2,935,522 | 5/1960 | Samour | 260/429.5 |
| 2,950,174 | 8/1960 | Legally | 260/429.5 X |
| 3,028,297 | 4/1962 | Legally | 260/429.5 X |
| 3,694,475 | 9/1972 | Brook et al. | 260/429.5 |
| 3,856,839 | 12/1974 | Smith et al. | 260/429.5 |
| 3,892,791 | 7/1975 | Brook et al. | 260/429.5 |
| 4,113,757 | 9/1978 | Kay | 260/429.5 |
| 4,159,209 | 6/1979 | Womersley | 260/429.5 X |
| 4,438,039 | 3/1984 | Beers et al. | 260/429.5 |

FOREIGN PATENT DOCUMENTS

| | | | |
|---|---|---|---|
| 2012924 | 9/1970 | Fed. Rep. of Germany | 260/429.5 |
| 2244462 | 5/1973 | Fed. Rep. of Germany | 260/429.5 |

*Primary Examiner*—Helen M. S. Sneed
*Attorney, Agent, or Firm*—Felfe & Lynch

[57] ABSTRACT

New titanium chelates containing triethanolamine as chelating agent, plus one or two glycol ether groups bound to the titanium atom are disclosed. Solutions of these new titanium chelates, pure or solved in glycol ether, can be diluted with water such that even 1% aqueous solutions are stable and show no turbidity or precipitation even after several weeks of standing. The new compounds are obtained by the reaction of the known triethanolamine titanates with glycol ethers, followed by distillation of the alcohol that forms, plus the alcohol serving as solvent, if any.

15 Claims, No Drawings

WATER-SOLUBLE TRIETHANOLAMINE TITANATES

The subject matter of the present invention is triethanolamine titanates which are stable even when greatly diluted with water and which cause no turbidity in dilute aqueous solutions.

The commercially available solutions of triethanolamine titanate are approximately 80% solutions of dialkoxy-di-triethanolaminotitanate which are obtained by the reaction of tetraalkoxytitanate with two moles of triethanolamine. The alkoxy group preferentially used is the isopropoxy group. The corresponding triethanolamine titanium chelate is in the form of a solution in isopropanol. These solutions find application, for example, in the thixotropation of dispersions, in the crosslinking of polymers containing hydroxyl groups, or in the cold coating of glass.

In many applications it is advantageous to use these triethanolamine titanate solutions in greatly diluted aqueous solution. Often only 1 to 2 wt.-% aqueous solutions are used. It is possible to dilute the known alcoholic triethanolamine titanate solutions with water, but the solutions obtained are not stable and rapidly become turbid, so that they are no longer usable for the desired purpose.

The problem therefore existed of finding triethanolamine titanates which are water-soluble and whose aqueous solutions are stable even in 1 wt.-% dilutions.

The obvious solution of this problem, namely first to dilute the known triethanolamine titanate solutions with alcohols or glycol ether to a titanium content of about 40 to 50 wt.-% and then perform the rest of the dilution with water, does not lead to the desired success, since the aqueous solutions obtained in this manner are not stable, either.

THE INVENTION

As the solution of the above-stated problem, triethanolamine titanates have been discovered which are characterized by a content of one or two glycol ether groups. These triethanolamine titanates or their solutions in glycol ethers are easily soluble in water and stable even in dilute aqueous solutions. Even solutions of 1 percent by weight display no turbidity even after standing for several months.

In the triethanolamine titanates of the invention, one or both of the alkoxy groups of the known dialkoxyditriethanolamine titanates is replaced by a glycol ether group. The new compounds can accordingly be referred to generally also as monoalkoxy-monoalkoxyalkylenoxy-bis(triethanolamine)titanates or as di-alkoxyalkylenoxy-bis(triethanolamine)titanates. The dialkoxyalkylenoxy compounds are the preferred compounds.

The new triethanolamine titanates are also easily soluble in glycol ethers. These solutions can easily be diluted with water to aqueous solutions containing less than 5 wt.-% of triethanolamine titanate, without the formation of a precipitate or the occurrence of turbidity in these solutions after long standing. In practice the use of such glycol ether solutions is recommendable, since they can be produced directly in the preparation of the new compounds.

The preparation begins either with the known titanium(IV) dialkoxy-di-triethanoamines or their alcoholic solutions. These are dissolved with as much glycol ether, one or two moles, as is necessary for the exchange of one or both alkoxy groups per mole of titanium compounds. Then the mixture is heated to temperatures of up to about 80° C. and the alcohol that has been formed is removed by distillation. The distillation is best performed in vacuo. If the triethanolamine titanate used as starting product is available as an alcoholic solution, the solvent alcohol is distilled out in addition to the alcohol that has formed.

In the preparation of the new triethanolamine titanates from the commercial dialkoxy-di-triethanolamine titanate solutions, which contain two moles of alcohol per mole of titanate, three moles of alcohol must accordingly be distilled out if it is desired to obtain the new mono-alkoxyalkylenoxytriethanolamine titanates. If both alkoxy groups of the starting compound are to be exchanged, four moles of alcohol must be removed from the mixture.

If the preparation of the new compounds in solvent-free form is desired, then, in the above-described type of procedure, only as many moles glycol ether is used as corresponds to the amount of moles bound alcohol that is to be exchanged. The distillation of the alcohol is then continued until both the originally bound alcohol and the simple alcohol used as solvent is distilled out.

It is also possible, however, and in many cases it is recommendable, in the process of producing the new titanates, to produce them in the form of solutions in glycol ether in a concentration which should amount to at least 40% for practical reasons. The procedure is then to add glycol ether in addition to the amount of glycol ether that is necessary for the exchange of the bound alcohol, in an amount corresponding to the desired concentration of the solution to be produced. Then, again both the bound alcohol contained in the starting product and the simple alcohol that may be contained as solvent are to be removed as entirely as possible.

It is furthermore also possible to prepare the new triethanolamine titanates by reacting the tetra-alkoxy-alkylenoxy titanate (from titanium tetrachloride by reaction with four moles of glycol ether) with two moles of triethanolamine, and then one has the choice of distilling out the glycol ether that is released or of utilizing the glycol ether solution directly.

In accordance with the invention, the term, "glcyol ethers," is to be understood to refer both to mono- and to polyglycol ethers which correspond to the general formula

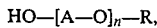

HO—[A—O]$_n$—R, wherein A represents ethylen or propylen moieties, R represents alkyl moieties of 1 to 4 carbon atoms, and n can assume values between 1 and 8, preferably between 1 and 4. Examples of such glycol ethers are glycol monomethyl ether, glycol monoethyl ether, glycol monoisopropylether, glycol monobutyl ether, propylenglycol monomethylether, diglycol monomethyl ether, diglycol monoethyl ether, diglycol monobutyl ether and dipropylenglycol monomethylether.

The hydroxyl groups in the above formula can also be replaced by an R'—C(O)—O group in which R' can be an alkyl group having 1 to 3 carbon atoms. Examples of such compounds, also known as glycol ether esters, are glycol monomethyl ether acetate or diglycol monobutyl ether acetate. These glycol ether esters are also generally called alkyl glycol carboxylates. These alkyl glycol carboxylates can be used either as solvents for the new triethanolamine titanates or they can serve for the introduction of the alkyl glycol moiety, giving likewise the same end products like the corresponding glycol ethers by transesterification.

The dialkoxy-di-triethanolamine titanate which is used preferentially for the preparation of the new titanates is diisopropoxy-di-triethanolamine, titanate, which is generally in the form of an 80% solution in isopropyl alcohol. However, other dialkoxytriethanolamine titanates can be used as starting compounds, in which the isopropoxy group is replaced, for example, by the n-butoxy, n-propoxy, isobutoxy or ethoxy group, and which are available in solution in the alcohols corresponding to the alkoxy groups.

The new titanium chelates of the invention are light yellow, viscous liquids. Their titanium content is of the order of magnitude of that of triethanolamine titanate (approx. 8.4% Ti). Dimethoxyethoxy-ethoxy-bis-triethanolaminotitanate contains 8.5% titanium.

The titanium chelates of the invention can be used wherever amine-containing titanates are usually used. Preferably, however, they are used wherever aqueous solutions are necessary in these known applications, such as, for example, in the crosslinking of resinous preparations which are used in aqueous solution as varnish binding agents. In such aqueous solutions they are, unlike the formerly known dialkoxy-bis-triethanolamine titanates, stable, do not lead to undesired precipitation or turbidity, and even in these dilute solutions they have crosslinking properties that are equal to, and often even better than, those of the known triethanolamine titanates.

The examples that follow will serve to describe a few ways of manufacturing and using the new titanium chelates, but the selection that has been made is not intended as a limitation of any of the possible variants.

EXAMPLE 1

Preparation of di-methoxyethoxyethoxy-bis-(triethanolamino)-titanium 291 g of commercial triethanolamine titanate (0.5 mol as 80% solution in isopropanol) is weighed into the one-liter flask of a laboratory vacuum rotary evaporator, and 120 g of methyl diglycol (1 mol, 2-(2-methoxyethoxy)ethanol) is added. Then, beginning at a water-bath temperature of 35° C., which is increased in the course of 6 hours to 80° C., and at a reduced pressure of 25 mbar, both the isopropanol present in the starting material and the isopropanol formed by the exchange reaction of the triethanolamine titanate with the methyl diglycol are distilled out. Yield of the removed alcohol: 119.4 g (99.5% of the theory = 120 g, 2 mol). The product thus obtained is a yellow, slightly viscous liquid of the following characteristics:

Index of refraction $n_D^{20} = 1.5190$
Viscosity (20° C.) = 264 mPa.s
Titanium dioxide content = 13.4%
Solubility: soluble in isopropanol, toluene and methylene chloride. 10% solutions in these solvents are stable over a period of at least three months.

EXAMPLE 2

Testing the solubility of the product of Example 1 in water-Comparison with conventional triethanolamine titanate

| Product | State of a solution containing 2.5% titanium chelate in desalted water |
|---|---|
| Per Example 1 | Clear solution, even after several weeks |
| Per Example 1, diluted with methyl diglycol to 50% | Clear solution, even after several weeks |
| Commercial triethanolamine titanate = 80% in isopropanol | Turbid solution |
| Triethanolamine titanate, diluted with isopropanol to 50% | Turbid solution |
| Triethanolamine titanate, diluted with methyldiglycol to 50% | Opalescent turbid solution |

EXAMPLE 3

Use of a titanium chelate of the invention as a crosslinking additive for a water-thinned varnish on the basis of acid phthalate resins A commercially available acid phthalate resin (Phthalopal LR 8525 ®, mfd. by BASF AG) is reacted in accordance with the following procedure to form a clear varnish:

250 g of this resin is dissolved in a mixture of 220 g of n-propanol, 500 g of water and 30 g of 2-amino-2-methyl-1-propanol. To this clear varnish, 2% of the titanium chelates listed in the following table was added in each case. The clear varnishes thus modified had the following stabilities:

| Additive | Appearance of the clear varnish after standing for 2 days |
|---|---|
| Titanium chelate of the invention as 50% solution in methyldiglycol | Clear, even after several weeks |
| Commercial triethanolamine titanate | Turbid after a few hours |

The crosslinking action of the titanium chelate additives was subjected to the MEK test after spreading the clear varnish on degreased aluminum and baking it on at 150° C. (45 minutes): The number of rubs with a cloth soaked in methyl ethyl ketone needed to remove the varnish film and conducted by hand serves as a measure of the crosslinking of the varnish coating. The following values were obtained:

| Clear varnish without additive | 1 rub |
|---|---|
| Clear varnish + titanium chelate of Example 1 | 85 rubs |
| Clear varnish + triethanolamine titanate | 71 rubs |

It will be understood that the specification and examples are illustrative but not limitative of the present invention and that other embodiments within the spirit and scope of the invention will suggest themselves to those skilled in the art.

What is claimed is:

1. A water-soluble bis-triethanolamine titanate having one or two glycol ether groups of the formula —O—[A—O]$_n$—R, wherein A is an ethylene or propylene moiety, R is an alkyl moiety of 1 to 4 carbon atoms, and n can assume values of 1 to 8.

2. The water-soluble bis-triethanolamine of claim 1, wherein n is 1 to 4.

3. A water-soluble titanate of claim 1 designated as dimethoxy-ethoxy-ethoxy-bis-(triethanolamino)-titanate(IV).

4. The water-soluble bis-triethanolamine titanate of claim 1 in solution in glycol ethers wherein the titanate content is between 40 and 99 weight-percent.

5. The water-soluble titanate of claim 3 in solution in glycol ethers wherein the titanate content is between 40 and 99 weight-percent.

6. The water-soluble triethanolamine titanate of claim 1 in solution in glycol ethers and water such that the titanate content is approximately 1–5%.

7. The water-soluble triethanolamine titanate of claim 3 in solution in glycol ethers and water such that the titanate content is approximately 1–5%.

8. The water-soluble bis-triethanolamine of claim 1 in solution in a glycol ether ester, wherein the titanium content is between 40 and 99 weight percent.

9. The water-soluble triethanolamine titanate of claim 4, wherein the glycol ether is selected from the group consisting of glycol monomethyl ether, glycol monoethyl ether, glycol monoisopropyl ether, glycol monobutyl ether, propylene glycol monomethyl ether, diglycol monomethyl ether, diglycol monoethyl ether, diglycol monobutyl ether and dipropylene glycol monoethyl ether.

10. The water-soluble triethanolamine titanate of claim 5, wherein the glycol ether is selected from the group consisting of glycol monomethyl ether, glycol monoethyl ether, glycol monoisopropyl ether, glycol monobutyl ether, propylene glycol monomethyl ether, diglycol monomethyl ether, diglycol monoethyl ether, diglycol monobutyl ether and dipropylene glycol monoethyl ether.

11. A method of preparing a water-soluble bis-triethanolamine titanate of claim 1 comprising reacting dialkoxy-bis-(triethanolamine)titanium(IV) with at least one equivalent of glycol ethers corresponding to the alkoxy group to form a reaction mixture, heating the reaction mixture and removing any formed alcohol and any alcohol solvent for the dialkoxy-bis-(triethanolamino)titanium.

12. A method of preparing a water-soluble bis-triethanolamine titanate of claim 1 comprising reacting dialkoxy-bis-(triethanolamine)titanium(IV) with at least one equivalent of a glycol ether ester corresponding to the alkoxy group and of the formula R'—C(O)—O[A—O]$_n$—R wherein R' is an alkyl group of 1 to 3 carbon atoms to form a reaction product, and transesterifying said reaction product to form the titanate.

13. The method of claim 12, wherein the glycol ether ester is selected from the group consisting of glycol monomethyl ether acetate and diglycol monobutyl ether acetate.

14. The method of claim 12, wherein n is 1 to 4.

15. A method of preparing bis-triethanolamine titanates containing glycol ether groups comprising reacting tetraalkoxyalkylenoxytitanates with triethanolamine and distilling out formed glycol monoether.

* * * * *